United States Patent [19]

Hester, Jr.

[11] Patent Number: 5,998,406

[45] Date of Patent: Dec. 7, 1999

[54] OXAZOLIDINONE DERIVATIVES AND PHARMACEUTICAL COMPOSITIONS

[75] Inventor: Jackson B. Hester, Jr., Galesburg, Mich.

[73] Assignee: Pharmacia & Upjohn Company, Kalamazoo, Mich.

[21] Appl. No.: 09/183,432

[22] Filed: Oct. 30, 1998

Related U.S. Application Data

[60] Provisional application No. 60/065,376, Nov. 12, 1997.

[51] Int. Cl.$^6$ .......................... A61K 31/55; C07D 243/00
[52] U.S. Cl. ............................................ 514/218; 540/492
[58] Field of Search .............................. 540/492; 514/218

[56] References Cited

U.S. PATENT DOCUMENTS

| | | | |
|---|---|---|---|
| 4,801,600 | 1/1989 | Wang et al. | 514/376 |
| 5,547,950 | 8/1996 | Hutchinson et al. | 514/252 |

FOREIGN PATENT DOCUMENTS

| | | |
|---|---|---|
| 0312000 | 10/1988 | European Pat. Off. . |
| 0316594 | 5/1989 | European Pat. Off. . |
| 0352781 | 1/1990 | European Pat. Off. . |
| WO90/02744 | 3/1990 | WIPO . |
| WO93/09103 | 5/1993 | WIPO . |
| WO93/23384 | 11/1993 | WIPO . |
| WO97/27188 | 7/1997 | WIPO . |

OTHER PUBLICATIONS

J. Med. Chem., 32, 1673–1681 (1989).
J. Med. Chem., 33, 2569–2578 (1990).
J. Med. Chem., 35, 1156 (1992).
Tetrahedron, 45, 1323–1326 (1989).

*Primary Examiner*—Mukund J. Shah
*Assistant Examiner*—Bruck Kifle
*Attorney, Agent, or Firm*—Lucy X. Yang

[57] ABSTRACT

A compound of Formula I:

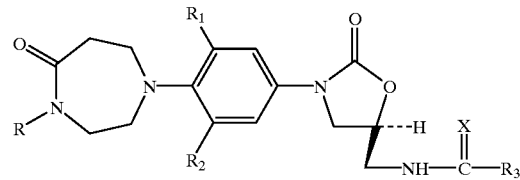

or a pharmaceutically acceptable salt thereof, which is antimicrobial agents, effective against various human and veterinary pathogens, including gram positive aerobic organisms, gram negative organisms, and anaerobic organisms.

10 Claims, No Drawings

OXAZOLIDINONE DERIVATIVES AND PHARMACEUTICAL COMPOSITIONS

CROSS-REFERENCE TO RELATED APPLICATIONS

This application claims the benefit of provisional application U.S. Ser. No. 60/065,376, filed Nov. 12, 1997.

BACKGROUND OF THE INVENTION

The present invention relates to novel oxazolidinone compounds or pharmaceutically acceptable salts thereof, and pharmaceutical agents that contain them as active ingredients for preventing or treating infectious diseases. The compounds are unique oxazolidinones having a hexahydro-1,4-diazepin-5-one substituent.

More specifically, novel oxazolidinone compounds of the present invention relates to useful antimicrobial agents, effective against various human and veterinary pathogens, including gram positive aerobic organisms such as multiply-resistant staphylococci and streptococci, gram negative organisms such as *H. influenzae* and *M. catarrhalis* as well as anaerobic organisms such as bacteroides and clostridia species, and acid-resistant organisms such as *Mycobacterium tuberculosis* and *Mycobacterium avium*.

INFORMATION DISCLOSURE

International Publication No. 97/27188 discloses piperazine-3-one analogs which are homologs of the invention.

International Publication No. WO93/23384 discloses oxazolidinones containing a substituted diazine (piperazine) moiety and their uses as antimicrobials.

International Publication No. WO93/09103 discloses substituted aryl and heteroaryl-phenyl-oxazolidinones useful as antimicrobials.

International Publication No. WO90/02744 discloses 5'-indolinyl-5-amidomethyloxazolidinones, 3-(fused-ring substituted)phenyl-5-midomethyloxazolidinones, and 3-(nitrogen substituted)-phenyl-5-amidomethyloxazolidinones which are useful as antibacterial agents.

Other references disclosing various oxazolidinones include U.S. Pat. No. 5,547,950, 4,801,600, *J. Med. Chem.*, 32,1673–81 (1989); *J. Med. Chem.*, 33, 2569–78 (1990); *Tetrahedron*, 45, 1323–26 (1989); and *J. Med. Chem.*, 35, 1156 (1992).

European Patent Publication 352,781 discloses phenyl and pyridyl substituted phenyl oxazolidinones.

European Patent Publication 316,594 discloses 3-substituted styryl oxazolidinones.

European Patent Publication 312,000 discloses phenylmethyl and pyridylmethyl substituted phenyl oxazolidinones.

SUMMARY OF THE INVENTION

The present invention provides an oxazolidinone derivative represented by the general structural Formula I or a pharmaceutically acceptable salt thereof

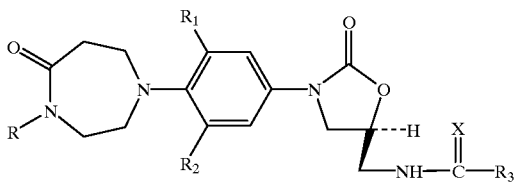

or a pharmaceutically acceptable salt thereof wherein:

R is H, $C_{2-6}$ alkenyl, $C_{2-7}$ alkynyl, $C_{1-6}$ alkyl, or $C_{1-6}$ alkyl substituted with one or two of the following:
a) F,
b) Cl,
c) $CF_3$,
d) —OH,
e) $C_{1-4}$ alkoxy,
f) —$CH_2C(=O)C_{1-4}$ alkyl,
g) —$OC(=O)N(R_4)_2$,
h) $C_{1-4}$ alkyl $S(O)_n$, (wherein n is 0 to 2),
I) —CN,
j) carboxy,
k) —$C_{1-4}$ alkoxycarbonyl,
l) —$C(=O)N(R_4)_2$,
m) —$N(R_4)SO_2C_{1-4}$ alkyl,
n) —$N(R_4)C(=O)C_{1-4}$ alkyl,
o) —$N(R_4)C(=O)N(R_4)_2$,
p) —$N(R_4)C(=O)C_{1-4}$ alkoxy,
q) aryl, or
r) Het;
aryl is phenyl, optionally substituted with one or two of the following:
a) F,
b) Cl,
c) Br,
d) —$CF_3$,
e) CN,
f) $C_{1-3}$ alkoxy, or
g) $C_{1-3}$ alkylthio;
Het is a 5- or 6-membered heteroaromatic moiety having 1-3 N, O or S atoms, optionally substituted with the following:
a) F,
b) Cl,
c) $C_{1-3}$ alkoxy,
d) $C_{1-3}$ alkylthio, or
e) CN;
$R_1$ and $R_2$ are independently H, F, or Cl; $R_3$ is
a) $C_{1-6}$ alkyl, optionally substituted with one to three F or one to two Cl,
b) $C_{1-6}$ alkoxy,
c) amino,
d) $C_{1-6}$ alkylamino,
e) $C_{1-6}$ dialkylamino
f) $C_{3-6}$ cycloalkyl,
g) $C_{1-6}$ alkylthio, or h)

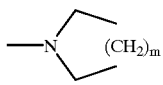

(wherein m is 0, 1, 2, 3 or 4); $R_4$ is
 a) H, or
 b) $C_{1-3}$ alkyl; and
X is O or S.

The present invention also provides an antimicrobial agent or pharmaceutical composition that contains the oxazolidinone compound or a pharmaceutically acceptable salt thereof as an active ingredient. The antimicrobial agent containing the active ingredient of the present invention can be used for treatment or prevention of infectious diseases.

DETAILED DESCRIPTION OF THE INVENTION

The compounds of Formula I as structurally disclosed above are useful antimicrobials. Typically, as further explained below, the compounds can be administered as antibacterial agents in a dosage range of from about 0.1 to 100 mg/kg or preferably from about 3.0 to about 50 mg/kg of body weight per day.

In the structural formula shown above the carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive.

The term "$C_{1-6}$ alkyl" used herein refers to an alkyl group having one to six carbon atoms such as, for example, methyl, ethyl, propyl, butyl, pentyl, hexyl and isomeric forms thereof; preferably methyl, ethyl, propyl and isomeric forms thereof.

The term "$C_{2-6}$ alkenyl" refers to at least one double bound alkenyl group having two to six carbon atoms such as, for example, vinyl, 1-propenyl, 2-propenyl, 2-methyl-1-propenyl, 1-butenyl, 2-butenyl, 1-pentenyl, 2-pentenyl, 1-hexenyl and isomeric forms thereof, preferably am alkenyl group having 2 to 6 carbon atoms, and more preferably an alkenyl group having 2 to 4 carbon atoms.

The term "$C_{2-7}$ alkynyl" refers to at least one triple bond alkynyl group having two to seven carbon atoms such as, for example, ethynyl, propynyl, butynyl, pentynyl, hexynyl, heptynyl and their isomeric forms thereof.

The term "$C_{1-6}$ alkylamino" refers to an alkyl group having one to six carbon atoms attached to an amino moiety.

The term "$C_{1-6}$ dialkylamino" refers to two alkyl groups having one to six carbon atoms attached to an amino moiety.

The term "$C_{1-4}$ alkoxy" refers to an alkyl group having one to four carbon atoms attached an oxygen atom of hydroxyl group such as, for example, methoxy, ethoxy, propoxy, butoxy and isomeric forms thereof, preferably an alkoxy group having 1 to 2 carbon atoms.

The term "$C_{1-6}$ alkylthio" refers to an alkyl group having one to six carbon atoms attached a thio moiety such as, for example, methythio, ethylthio, propylthio and isomeric forms thereof, preferably an alkylthio group having 1 to 2 carbon atoms.

The term "$C_{3-6}$ cycloalkyl" refers to three to six carbon atoms forming cyclopropyl, cyclobutyl, cyclopentyl, cyclohexyl and isomeric forms thereof.

The term "aryl" refers to an phenyl moiety optionally substituted with one or two F, Cl, Br, —$CF_3$, —CN, —$C_{1-3}$ alkoxy, or —$C_{1-3}$ alkylthio;

The term "Het" refers to a 5- or 6-membered heteroaromatic moiety having one to three atoms selected from the group consisting of O, N or S atoms such as, for example, furan, thiophene, pyrrole, pyrazole, triazoles, oxazole, thiazole, isothiazole, oxadiazoles, oxathiazole, pyridine, pyridazine, pyrimidine, pyrazine, piperazine and triazines all of which can optionally be substituted with one substituent selected from the group consisting of F, Cl, $C_{1-3}$ alkoxy, $C_{1-3}$ alkylthio or CN.

The compounds of the present invention can be converted to their salts according to conventional methods.

Pharmaceutically acceptable salts means acid addition salts useful for administering the compounds of this invention and these include hydrochloride, hydrobromide, sulfate, phosphate, acetate, propionate, lactate, mesylate, maleate, succinate, tartrate, citrate, 2-hydroxyethyl sulfonate, fumarate and the like when a basic group is present. These salts may be in hydrated form. Some of the compounds of this invention may form metal salts such as sodium, potassium, calcium and magnesium salts and these are embraced by the term "pharmaceutically acceptable salts".

Due to the configuration at C-5 of the oxazolidinone ring of compounds as represented in the structure of Formula I the compounds of this invention may exist in geometric, optical and other isomeric forms and this invention embraces any of these isomers. The racemic mixture and enantiomers are all believed to be useful as an antibacterial. Regardless, the preferred absolute configuration at C-5 of the oxazolidinone ring of compounds is as represented in the structure of Formula I. This absolute configuration is called (S) under the Cahn-Ingold-Prelog nomenclature system. It is believed that a majority of the pharmacological activity resides in this (S)-enantiomer to produce the antibacterial effect.

Compounds of Formula I can be prepared as shown in Scheme I where P represents an alcohol protecting group such as benzyl or tert-butyldimethylsilyl. Structure 2 of this scheme are prepared according to the methods outlined in Example 1, Step 1 and 2. In Scheme I, the alcohols of 2 are protected as benzyl ethers. In a suitable procedure for this reaction, a solution of the alcohol 2 in a solvent such as $Et_2O$ or THF is allowed to react first with sodium hydride at 0–25° C. and then with benzyl bromide and tetrabutylammonium iodide at 0–25° C. to give structure 3. The ethylene ketal of 3 can then be removed with an acidic catalyst such as p-toluenesulfonic acid in acetone (as described in Example 1, Step 2) to give structure 5 where P is benzyl. Alternatively the ketal of 2 can be removed, the resulting structure 4 is allowed to react with tert-butyldimethylsilyl chloride and imidazole in DMF or tert-butyldimethylsilyl chloride and triethyl amine in methylene chloride to give structure 5 where the alcohol protecting group (P) is tert-butyldimethylsilyl. Ketone 5 is then allowed to react with hydroxylamine hydrochloride and sodium acetate in methanol-methylene chloride to give oxime 6 (see Example 1, Step 3). The Beckmann rearrangement of structure 6 is carried out with p-toluenesulfonyl chloride and sodium carbonate in aqueous acetone at 20–40° C. to give structure 7. For compounds of Formula I where R is not hydrogen, compounds 7 can be alkylated with R'Y where Y is Br, I, $CH_3SO_3$ or p-$CH_3PhSO_3$ and R' is an appropriate alkyl substituent. In one method for this alkylation compounds of structure 7 are allowed to react with sodium hydride and R'Y in a solvent such as DMF at 0–25° C. to give 8. Alternatively, structure 7 can react with R'Y, potassium hydroxide and tetrabutylammonium bromide in THF or acetonitrile at 20–50° C. to give 8. Deprotection of the alcohols 7 or 8 provide structure 9. When P is a benzyl ether, this can be accomplished by hydrogenolysis with hydrogen and a palladium catalyst in ethanol or with ammonium formate and a palladium catalyst in methanol at 10–30° C. The tert-butyldimethylsilyl protecting group can be removed under acidic conditions or with fluoride ion. This deprotection can be carried out, for example, with trifluoroacetic acid in methylene chloride at 25° C. or with tetrabutylammonium fluoride in THF at 25° C. to give alcohol 9. Transformation of the alcohol 9 to the amine 11 can be carried out as described in Example 1, Step 1. Alternatively, the reaction of 9 with m-nitrobenzenesulfonyl chloride and triethylamine in methylene chloride at 5–25° C. will give the m-nitrobenzenesulfonate 10 which will react with ammonium hydroxide in THF or acetonitrile -isopropanol at 30–60° C. to give the amine 11. The reaction of compound 11 with acyl halides, anhydrides, isocyanates, isothiocyanates or dithioesters provides compounds of Formula I.

Compounds of Formula I where R is hydrogen and X is oxygen are conveniently prepared by allowing compounds 12 to react with p-toluenesulfonyl chloride and sodium carbonate in aqueous acetone at 20–40° C. (see Example 1, Step 4).

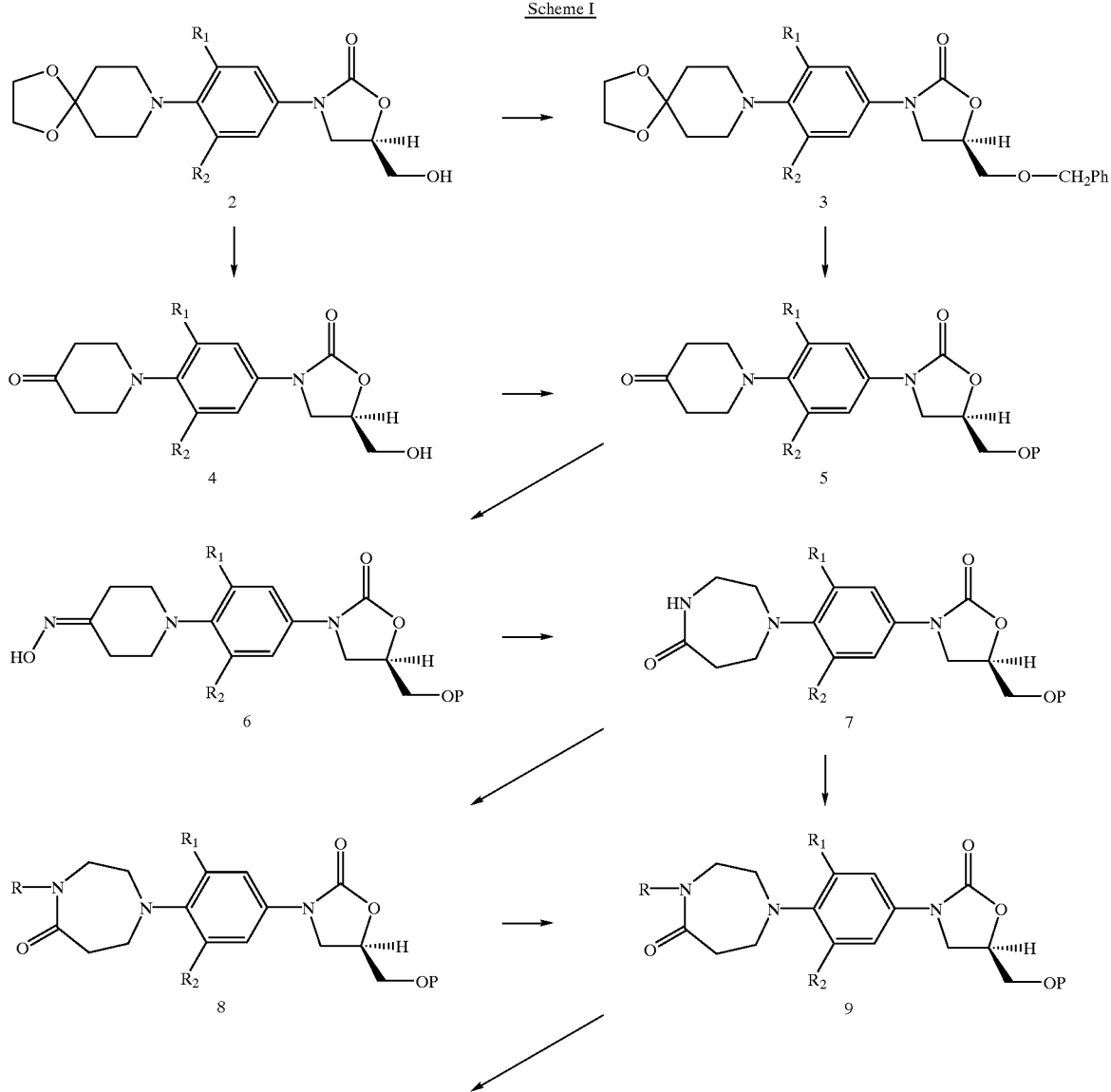

Scheme I

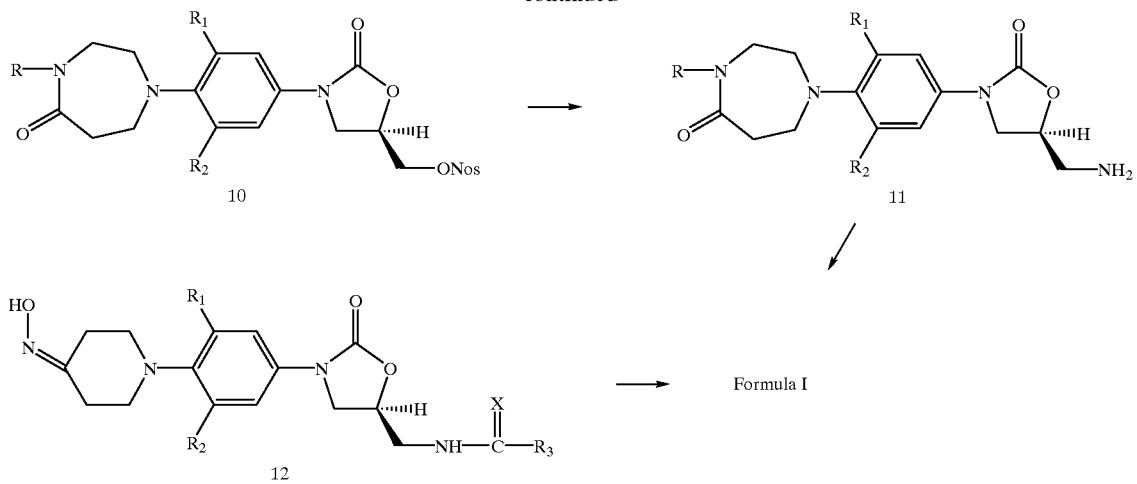

The compounds of the invention are useful for the treatment of microbial infections in humans and other warm blooded animals by either parenteral, oral, or topical administration.

The term "treatment" as used herein means partial or total lessening of symptoms of a disease which a patient suffers from; the term "prevention" as used herein means partial or total avoidance of symptoms of a disease in a patient who, according to a doctor's diagnosis, may suffer from the disease or a related state unless the preventive measure is taken.

The pharmaceutical compositions of this invention may be prepared by combining the compounds of Formula I of this invention with a solid or liquid pharmaceutically acceptable carrier and, optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing conventional coloring agents, flavoring agents, stabilizers and thickening agents.

Preferably, the pharmaceutical composition is made by employing conventional techniques in unit dosage form containing effective amounts of the active component, that is, the compound of Formula I according to this invention.

The quantity of active component, that is the compound of Formula I, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating, or combatting bacterial infections in humans and other animals that have been diagnosed with bacterial infections, the compounds or pharmaceutical compositions thereof will be administered orally, parenterally and/or topically at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100 mg/kg, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of Formula I are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (acid addition salt or base salt) dissolved in a pharmaceutically acceptable liquid carrier such as, for example, water-for-injection and a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine, to name a few. The compound according to Formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned antibacterially effective amount of dosage. The compounds of Formula I according to this invention are advantageously administered orally in solid and liquid dosage forms.

As a topical treatment, an effective amount of a compound of Formula I is admixed in a pharmaceutically acceptable gel or cream vehicle that can be applied to the patient's skin at the area of treatment. Preparation of such creams and gels is well known in the art and can include penetration enhancers.

The compounds of this invention are useful antimicrobial agents, effective against various human and veterinary pathogens, including gram positive aerobic organisms such as multiply-resistant staphylococci and streptococci, gram negative organisms such as *H. influenzae* and *M. catarrhalis* as well as anaerobic organisms such as bacteroides and clostridia species, and acid-resistant organisms such as *Mycobacterium tuberculosis* and *Mycobacterium avium*.

In order to more fully illustrate the nature of the invention and the manner of practice the same, the following experimental examples are presented, but they should not be taken as limitations.

EXAMPLE 1

Preparation of (S)-N-[[3-[3-fluoro-4-(1,2,3,4,6,7-hexahydro-5-oxo-1,4-diazepin-1-yl)phenyl]-2-oxo-5-oxazolidinyl]methyl]acetamide

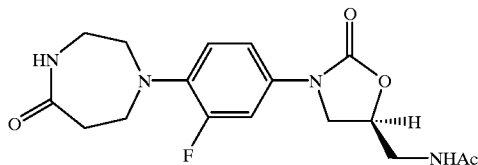

Step 1: Preparation of (S)-N-[3-(3-fluoro-4-piperidin-1-yl-phenyl)-2-oxo-oxazolidin-5-ylmethyl)-acetamide:

Diisopropylethylamine (15.7 ml) and 3,4-difluoronitrobenzene (5.0 ml) are added successively to an ethyl acetate solution (70 ml) of piperidine (5.77 g) and the mixture is stirred at room temperature for 2 days. Water is added to the reaction solution and the separating ethyl acetate layer are washed with water and brine, dried over anhydrous sodium sulfate. The solvent is evaporated to afford a nitro compound (10.1 g) in a yield of 100%. Palladium on carbon (10%, 1.0 g) is added to an ethyl acetate solution (101 ml) of the nitro compound (10.1 g) and the mixture is stirred at room temperature for 4 hours under hydrogen atmosphere. The palladium on carbon is filtered off and the filtrate is concentrated under vacuum to yield an amine (8.75 g, 100%). Sodium hydrogencarbonate (5.0 g) and benzyloxycarbonyl chloride (8.4 ml) are added successively to a tetrahydrofuran (THF) solution (100 ml) of the amine (8.75 g), and the mixture is stirred at room temperature for 14 hours. Water is added to the reaction solution and the separating THF layer is washed with water and brine, dried over anhydrous sodium sulfate. The solvent is evaporated and the residue is purified by silica gel column chromatography (solvent: ethyl acetate/hexane/chloroform=1/6/4) to afford a benzyl carbamate (14.5 g) in a yield of 98%. Butyl lithium (1.6 M hexane solution: 5.2 ml) is added to a THF solution (24 ml) of the benzyl carbamate (2.75 g) at −78 C. and the mixture is stirred for 5 min. At the same temperature, (R)-(−)-glycidyl butyrate (1.25 ml) is added to the stirred solution and the mixture is stirred for 14 hours while the temperature is raised slowly to room temperature. Water is added to the reaction solution and the separating THF layer is washed with water and brine, dried over anhydrous sodium sulfate. The solvent is evaporated and the residue is purified by silica gel column chromatography (solvent: ethyl acetate/hexane=3/1) to afford an alcohol (2.20 g) in a yield of 89%. Tosyl chloride (2.85 g) is added to a pyridine solution (8 ml) of the alcohol (2.20 g) and the mixture is stirred at room temperature for 6 h. Water (32 ml) is added to the reaction solution and the mixture is stirred for 1 hour. The resulting precipitate is collected by filtration and washed with water, followed by drying under vacuum at room temperature to afford a tosylate (3.28 g) in a yield of 98%. Sodium azide (3.80 g) is added to a dimethylformamide (DMF) solution (23 ml) of the tosylate (3.28 g) at room temperature and the mixture is stirred at 65 C. for 5.5 hours. After the reaction mixture is cooled to room temperature, water is added and the mixture is extracted with ethyl acetate; the organic layer is concentrated under vacuum. The resulting residue is dissolved in ethyl acetate and washed with water and brine, dried over anhydrous sodium sulfate. The solvent is evaporated and the residue is purified by silica gel column chromatography (solvent: ethyl acetate/hexane=1/1) to afford an azide (2.20 g) in a yield of 94%. Acetic anhydride (0.65 ml) and pyridine (1.0 ml) are added to an ethyl acetate solution (19 ml) of the azide (2.20 g) at room temperature; after addition of palladium on carbon (10%, 0.22 g), the mixture is stirred at room temperature for 6 hours under 1 atm hydrogen atmosphere. The palladium on carbon is filtered off and the filtrate is washed with water and brine, dried over anhydrous sodium sulfate. The solvent is evaporated and the residue is purified by silica gel column chromatography (solvent: acetone/hexane=1/1) to afford the title compound.

Step 2: Preparation of (S)-N-{3-[3-fluoro-4-(4-oxo-piperidin-1-yl)-phenyl]-2-oxo-oxazolidin-5-ylmethyl}-acetamide.

Using a commercially available 1,4-dioxo-8-aza-spiro [4.5]decane, (S)-N-{3-[4-(1,4-dioxa-8-aza-spiro[4.5]dec-8-yl)-3-fluoro-phenyl]-2-oxo-oxazolidin-5-ylmethyl}- acetamide is synthesized by the same method as in Step 1. To an acetone solution (70 ml) of this compound (3.79 g), water (20 ml) and p-toluenesulfonic acid monohydrate (3.66 g) are added successively and the mixture is heated under reflux for 3 hours. After the reaction mixture is cooled to room temperature, acetone is distilled off and the aqueous layer is neutralized with triethylamine. The solution is extracted with methylene chloride and the organic layer is washed with brine, dried over anhydrous sodium sulfate. The solvent is evaporated and the residue is purified by silica gel column chromatography (solvent: chloroform/methanol=50/1-25/1) to afford the title compound.

Step 3: Preparation of (S)-N-{3-[3-fluoro-4-(4-hydroxyimino-piperidin-1-yl)-phenyl]-2-oxo oxazolidin-5-ylmethyl}-acetamide.

Sodium acetate (517 mg) and hydroxylamine hydrochloride (219 mg) are successively added to a methanol-methylene chloride solution (10—10 ml) of 1.00 g of the product of Step 2, and the mixture is stirred at room temperature for 2 days. The solvent is evaporated and the residue is dissolved in methanol, followed by addition of a silica gel (8 g). Methanol is evaporated and the residue is purified by silica gel column chromatography (solvent: chloroform/methanol=50/1-25/1) to afford the title compound.

Step 4: Preparation of (S)-N-[[3-[3-Fluoro-4-(1,2,3,4,6,7-hexahydro-5-oxo-1,4-diazepin-1-yl)phenyl]-2-oxo-5-oxazolidinyl]methyl]acetamide.

A stirred mixture of the compound of product of Step 3 (0.200 g, 0.549 mmol) in acetone (5.3 mL), under nitrogen, is treated first with 5% aqueous sodium carbonate (5.3 mL) and then, dropwise during 3minutes with a solution of p-toluenesulfonyl chloride (0.16 g, 0.82 mmol) in acetone (2.7 mL). Initially this mixture is a two phase solution; however, after about 25minutes a precipitate began to form. It is kept at ambient temperature (23° C.) for 4 hours and filtered. The filtrate is concentrated under reduced pressure to remove acetone and the aqueous residue is extracted with $CH_2Cl_2$. The extract is dried ($MgSO_4$) and concentrated to give a small amount of crude product. Most of the product is in the aqueous layer which is concentrated in vacuo. The residue is combined with the crude product from the $CH_2Cl_2$ extract and chromatographed on silica gel with mixtures of $MeOH—NH_4OH—CH_2Cl_2$ that continued 3–5% MeOH and 0.3–0.5% $NH_4OH$. The product is crystallized from MeOH—EtOAc to give the title compound. mp 140–146° C.;

MS m/z (relative intensity)364($M^+$, 96.1), 320(100), 306 (6.7), 294(10.9), 236(41.8);

HRMS calcd for $C_{17}H_{21}FN_4O_4$; 364.1547 ($M^+$); found 364.1545;

$^1$H NMR [300 MHz, $(CD_3)_2SO$] δ 1.81 (s, 3H), 2.57(m, 2H), 3.07(m, 4H), 3.24 (m, 2H), 3.38 (t, 2H), 3.67(d, d, 1H), 4.06(t, 1H), 4.68(m, 1H), 7.08(t, 1H), 7.13 (d, d, 1H), 7.45 (d, d, 1H), 7.65 (t, 1H), 8.21 (t, 1H).

EXAMPLE 2

Preparation of (S)-N-[[3-[3-fluoro-4-(1,2,3,4,6,7-hexahydro-5-oxo-1,4-diazepin-1-yl)phenyl]-2-oxo-5-oxazolidinyl]methyl]thioacetamide.

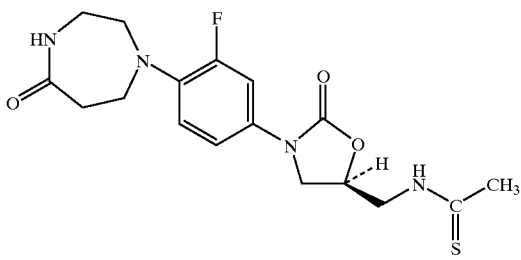

Step 1: Preparation of (S)-[3-[3-fluoro-4-(1,2,3,4,6,7-hexahydro-5-oxo-1,4-diazepin-1-yl)-phenyl]-2-oxo-5-oxazolidinyl]methyl tert-butyldimethylsilyl ether.

A stirred solution of 10.6 g (0.03 mol) of (S)-[3-[4-(1,4-dioxo-8-azaspiro[4.5]dec-8-yl)-3-fluorophenyl]-2-oxo-5-oxazolidinyl]methanol, the intermediate of formula 2 (Scheme 1) for the preparation of (S)-N-{3-[3-fluoro-4-(4-oxopiperidin-1-yl)phenyl]-2-oxooxazolidin-5-ylmethyl}-acetamide (Example 1, Step 2), in acetone (230 mL) is treated with water (65 mL) and p-toluenesulfonic acid monohydrate (11.4 g, 0.06 mol), refluxed under nitrogen for 5 hours and kept at ambient temperature (24° C.) for 18 hours. It is then concentrated in vacuo to remove acetone. The aqueous residue is neutralized with sodium bicarbonate and extracted with ethyl acetate; the extract is washed with saturated sodium bicarbonate, water and dilute sodium chloride, dried ($Na_2SO_4$) and concentrated to give the ketone, a compound of formula 4 (Scheme 1). A stirred solution of the ketone and triethylamine (12.5 mL, 0.09 mol) in methylene chloride (100 mL) is treated with tert-butyldimethylsilyl chloride (6.03 g, 0.04 mol) and kept under nitrogen at ambient temperature for 23 hours. Additional tert-butyldimethylsilyl chloride (3.0 g) is added and the mixture is kept at ambient temperature for an additional 20 hours. Additional triethylamine (3.0 mL) and tert-butyldimethylsilyl chloride (3.0 g) are again added and the mixture is kept at ambient temperature for 4 days, diluted with methylene chloride, washed with water and dilute sodium chloride, dried ($Na_2SO_4$) and concentrated. Chromatography of the residue on silica gel with mixtures of acetone-heptane that contained 20–30% acetone gave 7.72 g of the tert-butyldimethylsilyl (TBDMS) ether, a compound of formula 5 (Scheme 1) where P is TBDMS. A stirred solution of the TBDMS ether (7.27 g, 17.2 mmol) in methanol (150 mL) is treated dropwise with a solution of hydroxylamine hydrochloride (1.44 g, 0.021 mol) and sodium acetate (1.72 g, 0.021 mol) in water (15 mL) and kept at ambient temperature for 20 hours. The mixture is concentrated under reduced pressure. A solution of the residue, a white solid, in methylene chloride is washed with water and dilute sodium chloride, dried ($Na_2SO_4$) and concentrated to give 7.25 g of the oxime, a compound of formula 6 (Scheme 1). A stirred solution of the oxime in acetone (165 ML), under nitrogen, is treated with 5% aqueous sodium carbonate (165 mL) and then dropwise during 20 minutes with a solution of p-toluenesulfonyl chloride (4.92 g, 0.0258 mol) in acetone (80 mL). The mixture is kept at ambient temperature for 18 hours and then concentrated under reduced pressure. A solution of the residue in methylene chloride is washed with water and dilute sodium chloride, dried ($Na_2SO_4$) and concentrated. Chromatography of the residue on silica gel with 3% methanol-0.3% ammonium hydroxide-methylene chloride gave 5.98 g of the titled compound.

Step 2: Preparation of (S)-[[3-[3-fluoro-4-(1,2,3,4,6,7-hexahydro-5-oxo-1,4-diazepin-1-yl)phenyl]-2-oxo-5-oxazolidinyl]methyl]amine.

An ice cold, stirred mixture of the product of Example 2, Step 1 (0.22 g, 0.50 mmol) in tetrahydrofuran (THF; 15 mL), under nitrogen, is treated dropwise during 2 minutes, with a 1M solution of tetrabutylammonium fluoride in THF (1.5 mL). The mixture is kept in the ice bath for 10 minutes and at ambient temperature (24° C.) for 1 hour 25 minutes, diluted with ethyl acetate, washed with water and brine, dried (Na2SO4) and concentrated. Chromatography of the residue on silica gel with mixtures of 25 methanol-methylene chloride containing 3–6% methanol gave 0.15 g of the alcohol, a compound of formula 9 (Scheme 1) where R is hydrogen: MS(ES) m/z 324 ($M+H^+$). A stirred suspension of the alcohol (0.15 g, 0.46 mmol) in methylene chloride (15 mL) and THF (8 mL), under nitrogen, is treated with triethylamine (0.5 mL, 1.4 mmol) and then portionwise during 1 minute at ambient temperature, with 0.14 g (0.56 mmol) of m-nitrobenzenesulfonyl chloride. The mixture is stirred for 90 minutes, mixed with additional methylene chloride (10 mL) to give a solution and kept at ambient temperature for 1 hour. It is then kept for several days at −11° C., diluted with methylene chloride, washed with saturated sodium bicarbonate, water and brine, dried ($Na_2SO_4$) and concentrated to give 0.21 g of the m-nitrobenzenesulfonate, a compound of formula 10 (Scheme 1). A stirred mixture of the m-nitrobenzenesulfonate (0.21 g, 0.44 mmol), acetonitrile (10 mL), 2-propanol (10 mL) and 29% ammonium hydroxide (10 mL) is warmed at 45–50° C. under a Dry Ice-acetone condenser for 4.5 hours and kept at ambient temperature for 18 hours. Additional ammonium hydroxide (5 mL) is added and the mixture is warmed at 45–50° C. for 4.5 hours, kept at ambient temperature for 1 hour, treated with 5 mL of ammonium hydroxide and kept at ambient temperature for 18 hours. It is then concentrated to give a yellow solid which is chromatographed on silica gel with mixtures of methanol-methylene chloride containing 5–7.5% methanol followed by 8% methanol-0.2% ammonium hydroxide-methylene chloride to give the titled product.

Step 3: Preparation of (S)-N-[[3-[3-fluoro-4-(1,2,3,4,6,7-hexahydro-5-oxo-1,4-diazepin-1-yl)phenyl]-2-oxo-5-oxazolidinyl]methyl]thioacetamide.

A stirred solution of 0.12 g of the product of Example 2, Step 2 and 0.40 mL of triethylamine in a mixture of methylene chloride (10 mL) and methanol (10 mL), under nitrogen, is treated with ethyl dithioacetate (0.05 mL) and kept at ambient temperature for 145 hours. Additional 0.05 mL portions of ethyl dithioacetate are added after 24, 31 and 49 hours; additional triethylamine (1.0 mL) is also added after 49 hours. The mixture is concentrated to a small volume, diluted with ethyl acetate, washed with water and brine, dried ($Na_2SO_4$) and concentrated. Chromatography of the residue on silica gel with 3.5% methanol-methylene chloride gave 0.061 g of the titled product.

$^1$H NMR [300 MHz, $(CD_3)_2SO$] δ 2.42(s, 3H), 2.56(m, 2H), 3.07(m, 4H), 3.24(m, 2H), 3.76(dd, 1H), 3.87(m, 2H), 4.11(t, 1H), 4.91(m, 1H), 7.12(m, 2H), 7.46(dd, 1H), 7.67 (broad s, 1H), 10.35(broad s, 1H).

EXAMPLE 3

Preparation of (S)-N-[[3-[3-fluoro-4-(1,2,3,4,6,7-hexahydro-4-methyl-5-oxo-1,4-diazepin-1-yl)phenyl]-2-oxo-5-oxazolidinyl]methyl]-acetamide.

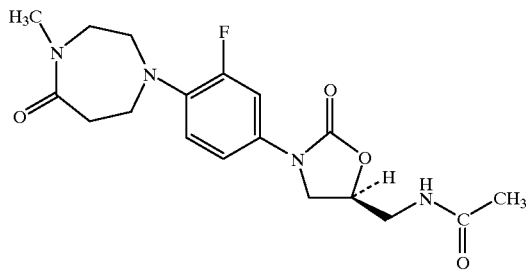

Step 1: Preparation of (S)-[[3-[3-fluoro-4-(1,2,3,4,6,7-hexahydro-4-methyl-5-oxo-1,4-diazepin-1-yl)phenyl]-2-oxo-5-oxazolidinyl]methyl]amine.

A mixture of 0.63 g (1.4 mmol) of the product of Example 2, Step 2, methyl iodide (0.093 mL) and THF (40 mL) is added dropwise during 12 minutes, under nitrogen, to a stirred mixture of powdered potassium hydroxide (0.12 g) and tetrabutylammonium bromide (0.096 g) in THF (10 mL) and kept at ambient temperature for 20 hours. It is then diluted with ethyl acetate, washed with water and brine, dried ($MgSO_4$) and concentrated. Chromatography of the residue on silica gel with mixtures of acetone-methylene chloride that contained 10–40% acetone gave 0.46 g (71%) of the methylated product, a compound of formula 8 (Scheme 1) where R' is methyl. An ice cold, stirred mixture of this product (0.17 g, 0.38 mmol) and THF (12 mL), under nitrogen, is treated dropwise with a 1M solution of tetrabutylammonium fluoride in THF (1.2 mL). It is kept in the ice bath for 15 minutes and at ambient temperature for 3 hours, mixed with ice water and extracted with ethyl acetate. The extract is washed with water and brine, dried ($MgSO_4$) and concentrated to give 0.15 g of the alcohol, a compound of formula 9 (Scheme 1). A stirred, ice cold solution of the alcohol (0.52 g, 1.5 mmol) and triethylamine (0.60 mL) in methylene chloride (45 mL) is treated portionwise during 5 minutes with m-nitrobenzenesulfonyl chloride (0.42 g). The mixture is kept in the ice bath for 15 minutes and at ambient temperature for 3 hours, diluted with methylene chloride, washed with saturated sodium bicarbonate, water and brine, dried ($MgSO_4$) and concentrated to give the m-nitrobenzenesulfonate, a compound of formula 10 (Scheme 1). A stirred mixture of this product, acetonitrile (35 mL), 2-propanol (35 mL) and concentrated ammonium hydroxide (35 mL) is kept at 45–50° C. under a Dry Ice-acetone condenser for 4.5 hours and at ambient temperature for 20 hours. Additional ammonium hydroxide (6 mL) is added and the mixture is kept at 45–50° C. for 5.5 hours and at ambient temperature for 18 hours. The mixture is then concentrated under reduced pressure to remove the organic solvents and the aqueous residue is extracted first with ethyl acetate and then methylene chloride. The extracts are washed with water and brine, dried ($MgSO_4$) and concentrated. Chromatography of the residue on silica gel with mixtures of methanol-methylene chloride containing 7.5–10% methanol gave the titled compound.

Step 2: Preparation of (S)-N-[[3-[3-fluoro-4-(1,2,3,4,6,7-hexahydro-4-methyl-5-oxo-1,4-diazepin-1-yl)phenyl]-2-oxo-5-oxazolidinyl]methyl]acetamide.

A stirred, ice cold mixture of 0.10 g (0.30 mmol) of the product of Example 3, Step 1, and pyridine (1.74 mL), under nitrogen, is treated dropwise with acetic anhydride (0.57 mL, 6.04 mmol) and kept in the ice bath for 15 minutes and at ambient temperature for 3.5 hours. It is then concentrated in vacuo; the residue is mixed with ice water and saturated sodium bicarbonate and extracted with ethyl acetate. The extract is washed with water and brine, dried ($MgSO_4$) and concentrated. Crystallization of the residue from ethyl acetate-methanol gave 0.053 g of the titled compound.

mp 203–204° C.

MS(ES) m/z 379 (M+H$^+$), 401 (M+Na$^+$).

Anal. calcd for $C_{18}H_{23}FN_4O_4$: C, 57.13; H, 6.13; N, 14.81. Found: C, 57.05; H, 6.23; N, 14.85.

EXAMPLE 4

Preparation of (S)-N-[[3-[3-fluoro-4-(1,2,3,4,6,7-hexahydro-4-methyl-5-oxo-1,4-diazepin-1-yl)phenyl]-2-oxo-5-oxazolidinyl]methyl]-thioacetamide.

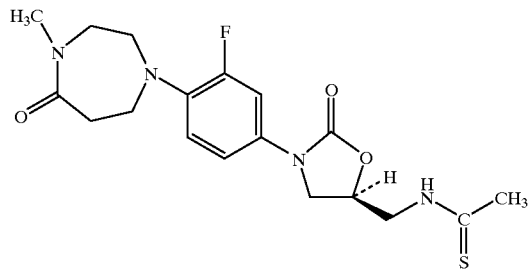

An ice cold, stirred solution of 0.18 g (0.535 mmol) of the product of Example 3, Step 1 and triethylamine (0.21 mL) in THF (8 mL) and methylene chloride (10 mL) is treated with a solution of ethyl dithioacetate (0.074 mL, 0.64 mmol) in THF (2 mL). The mixture is kept at ambient temperature for 20 hours, treated with one drop of additional ethyl dithioacetate and kept at ambient temperature for 7 hours. It is then concentrated under a stream of nitrogen. The residue is mixed with methylene chloride, washed with saturated sodium bicarbonate, water and brine, dried ($Na_2SO_4$) and concentrated. Chromatography of the residue on silica gel with mixtures of methanol-methylene chloride containing 2–4% methanol and crystallization of the product from ethyl acetate gave 0.13 g of the titled compound. mp 157–158° C.

Anal. calcd for $C_{18}H_{23}FN_4O_3S$: C, 54.81; H, 5.88; N, 14.20. Found: C, 54.83; H, 5.93; N, 14.11.

EXAMPLE 5

MIC Test Method

The in vitro MICs of test compounds are determined by a standard agar dilution method. A stock drug solution of each analog is prepared in the preferred solvent, usually DMSO:$H_2O$(1:3). Serial 2-fold dilutions of each sample are made using 1.0 ml aliquots of sterile distilled water. To each 1.0 ml aliquot of drug is added 9 ml of molten Mueller Hinton agar medium. The drug-supplemented agar is mixed, poured into 15×100 mm petri dishes, and allowed to solidify and dry prior to inoculation.

Vials of each of the test organisms are maintained frozen in the vapor phase of a liquid nitrogen freezer. Test cultures are grown overnight at 35 C. on the medium appropriate for the organism. Colonies are harvested with a sterile swab, and cell suspensions are prepared in Trypticase Soy broth (TSB) to equal the turbidity of a 0.5 McFarland standard. A 1:20 dilution of each suspension is made in TSB. The plates containing the drug supplemented agar are inoculated with a 0.001 ml drop of the cell suspension using a Steers replicator, yielding approximately $10^4$ to $10^5$ cells per spot. The plates are incubated overnight at 35 C.

Following incubation the Minimum Inhibitory Concentration (MIC μg/ml), the lowest concentration of drug that inhibits visible growth of the organism, is read and recorded. The data is shown in Table I.

TABLE I

| Example No. | SAUR[a] 9213 MIC | SEPI[b] 12084 MIC | EFAE[c] 9217 MIC | SPNE[d] 9912 MIC | HINF[e] 30063 MIC | MCAT[f] 30610 MIC |
|---|---|---|---|---|---|---|
| 1 | 4 | 1 | 4 | 0.5 | 8 | 8 |
| 3 | 4 | 1 | 4 | 1 | 32 | 8 |
| 4 | 1 | <0.5 | 1 | <0.5 | 8 | 2 |

[a]) *S. aureus*, culture 9213
[b]) *S. epidermidis*, culture 12084
[c]) *E. faecalis*, culture 9217
[d]) *S. pueumoniae*, culture 9912
[e]) *H. influenzae*, culture 30063
[f]) *M. catarrhalis*, culture 30610

What is claimed is:

1. A compound of Formula I:

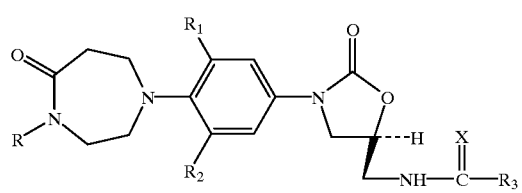

I or a pharmaceutically acceptable salt thereof wherein: R is H, $C_{2-6}$ alkenyl, $C_{2-7}$ alkynyl, $C_{1-6}$ alkyl, or $C_{1-6}$ alkyl substituted with one or two of the following:

a) F,
b) Cl,
c) $CF_3$,
d) —OH,
e) $C_{1-4}$ alkoxy,
f) —$CH_2C(=O)C_{1-4}$ alkyl,
g) —$OC(=O)N(R_4)_2$,
h) $C_{1-4}$ alkyl $S(O)_n$, (wherein n is 0, 1 or 2),
i) —CN,
j) carboxy,
k) —$C_{1-4}$ alkoxycarbonyl,
l) —$C(=O)N(R_4)_2$,
m) —$N(R_4)SO_2C_{1-4}$ alkyl,
n) —$N(R_4)C(=O)C_{1-4}$ alkyl,
o) —$N(R_4)C(=O)N(R_4)_2$,
p) —$N(R_4)C(=O)C_{1-4}$ alkoxy,
q) aryl, or
r) Het;

aryl is phenyl, optionally substituted with one or two of the following:

a) F,
b) Cl,
c) Br,
d) —$CF_3$,
e) CN,
f) $C_{1-3}$ alkoxy, or
g) $C_{1-3}$ alkylthio;

Het is a 5- or 6-membered heteroaromatic moiety having 1–3 N , O or S atoms, optionally substituted with the following:

a) F,
b) Cl,
c) $C_{1-3}$ alkoxy,
d) $C_{1-3}$ alkylthio, or
e) CN;

$R_1$ and $R_2$ are independently a) H,
b) F,or
c) Cl;

$R_3$ is a) $C_{1-6}$ alkyl, optionally substituted with one to three F or one to two Cl,
b) $C_{1-6}$ alkoxy,
c) amino,
d) $C_{1-6}$ alkylamino,
e) $C_{1-6}$ dialkylamino
f) $C_{3-6}$ cycloalkyl,
g) $C_{1-6}$ alkylthio, or
h)

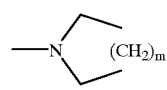

(wherein m is 0, 1, 2, 3 or 4);

$R_4$ is a) H, or
b) $C_{1-3}$ alkyl; and

X is O or S.

2. A compound of claim 1 wherein X is O.
3. A compound of claim 1 wherein X is S.
4. A compound of claim 1 wherein R is H.
5. A compound of claim 1 wherein R is $C_{1-4}$ alkyl.
6. A compound of claim 1 wherein $R_3$ is $C_{1-4}$ alkyl, optionally substituted with one to three F or one to two Cl.
7. The compound of claim 1 wherein Formula I is the S-enantiomer.
8. A compound of claim 1 which is
   (a) (S)-N-[[3-[3-fluoro-4-(1,2,3,4,6,7-hexahydro-5-oxo-1,4-diazepin-1-yl)phenyl]-2-oxo-5-oxazolidinyl]methyl]acetamide,
   (b) (S)-N-[[3-[3-fluoro-4-(1,2,3,4,6,7-hexahydro-5-oxo-1,4-diazepin-1-yl)phenyl]-2oxo-5-oxazolidinyl]methyl]thioacetamide,
   (c) (S)-N-[[3-[3-fluoro-4-(1,2,3,4,6,7-hexahydro-4-methyl-5-oxo-1,4-diazepin-1-yl)phenyl]-2-oxo-5-oxazolidinyl]methyl]acetamide, or
   (d) (S)-N-[[3-[3-fluoro-4-(1,2,3,4,6,7-hexahydro-4-methyl-5-oxo-1,4-diazepin-1-yl)phenyl]-2-oxo-5-oxazolidinyl]methyl]thioacetamide.

9. A method for treating microbial infections in human comprising administering to a patient in need thereof an effective amound of a compound of Formula I as shown in claim 1.

10. A pharmaceutical composition comprising a compound of Formula I as shown in claim 1 and a pharmaceutically acceptable carrier.

* * * * *